US00PP20178P2

(12) United States Plant Patent
Kaagman

(10) Patent No.: US PP20,178 P2
(45) Date of Patent: Jul. 14, 2009

(54) ***OSTEOSPERMUM* PLANT NAMED 'TRA YELBIC'**

(50) Latin Name: *Osteospermum ecklonis*
Varietal Denomination: Tra Yelbic

(75) Inventor: Pim Kaagman, Andijk (NL)

(73) Assignee: Goldsmith Seeds Europe B.V., Andijk (NL)

( * ) Notice: Subject to any disclaimer, the term of this patent is extended or adjusted under 35 U.S.C. 154(b) by 0 days.

(21) Appl. No.: 12/080,553

(22) Filed: Apr. 3, 2008

(51) Int. Cl.
*A01H 5/00* (2006.01)

(52) U.S. Cl. ..... Plt./360
(58) Field of Classification Search ..... Plt./360
See application file for complete search history.

*Primary Examiner*—S. B McCormick Ewoldt
(74) *Attorney, Agent, or Firm*—C. A. Whealy

(57) ABSTRACT

A new and distinct cultivar of *Osteospermum* plant named 'Tra Yelbic', characterized by its compact plant habit; freely branching growth habit; dense and full plants; early and freely flowering habit; large daisy-type inflorescences with white-colored ray florets with yellow-colored apices; and good garden performance.

2 Drawing Sheets

Botanical designation: *Osteospermum ecklonis.*
Cultivar denomination: 'Tra Yelbic'.

Referenced to closely-related applications: Title: *Osteospermum* Plant Named 'Tra Tercot'. Applicant: Pim Kaagman. U.S. Plant pantent application Ser. No. 12/080,554: Filed concurrently with this application.

BACKGROUND OF THE INVENTION

The present invention relates to a new and distinct cultivar of *Osteospermum* plant, botanically known as *Osteospermum ecklonis,* and hereinafter referred to by the name 'Tra Yelbic'.

The new *Osteospermum* is a product of a planned breeding program conducted by the Inventor in Andijk, The Netherlands. The objective of the program is to create and develop new compact *Osteospermum* cultivars with uniformly mounded plant habit, early and freely flowering habit and attractive ray and disc floret coloration.

The new *Osteospermum* originated from a cross-pollination conducted by the Inventor in Andijk, The Netherlands in June, 1999 of a proprietary selection of *Osteospermum ecklonis* identified as code number OZ-185-1, not patented, as the female, or seed, parent with a proprietary selection of *Osteospermum ecklonis* identified as code number OY-81-2, not patented, as the male, or pollen, parent. The new *Osteospermum* was discovered and selected by the Inventor as a single flowering plant within the progeny of the stated cross-pollination in a controlled environment in Andijk, The Netherlands in January, 2004.

Asexual reproduction of the new *Osteospermum* by terminal cuttings in a controlled environment in Andijk, The Netherlands since January, 2004, has shown that the unique features of this new *Osteospermum* are stable and reproduced true to type in successive generations.

SUMMARY OF THE INVENTION

Plants of 'Tra Yelbic' have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Tra Yelbic'. These characteristics in combination distinguish 'Tra Yelbic' as a new and distinct cultivar of *Osteospermum:*

1. Compact plant habit.
2. Freely branching growth habit; dense and full plants.
3. Early and freely flowering habit.
4. Large daisy-type inflorescences with white-colored ray florets with yellow-colored apices.
5. Good garden performance.

Plants of the new *Osteospermum* differ from plants of the female parent selection in the following characteristics:

1. Plants of the new *Osteospermum* are more freely branching than plants of the female parent selection.
2. Inflorescences of plants of the new *Osteospermum* are flatter and more open than inflorescences of plants of the female parent selection.
3. Plants of the new *Osteospermum* and the female parent selection differ in ray floret color as ray florets of plants of the female parent selection are lemon yellow in color.

Plants of the new *Osteospermum* differ from plants of the male parent selection in the following characteristics:

1. Plants of the new *Osteospermum* are more compact than plants of the male parent selection.
2. Plants of the new *Osteospermum* has larger inflorescences than plants of the male parent selection.
3. Plants of the new *Osteospermum* and the male parent selection differ in ray floret color as ray florets of plants of the male parent selection are purple in color.

Plants of the new *Osteospermum* can be compared to plants of the *Osteospermum* 'Tra Tercot', U.S. Plant patent application Ser. No. 12/080,554 filed concurrently. Plants of the new *Osteospermum* differ primarily from plants of 'Tra Tercot' in ray floret color as plants of 'Tra Tercot' have salmon-colored ray florets. In addition, plants of the new *Osteospermum* have larger leaves than plants of 'Tra Tercot'.

Plants of the new *Osteospermum* can be compared to plants of the *Osteospermum* 'Sunny Amanda', disclosed in U.S. Plant Pat. No. 16,522. In side-by-side comparisons conducted in Hillscheid, Germany, plants of the new *Osteospermum* differed from plants of 'Sunny Amanda' in the following characteristics:

1. Plants of the new *Osteospermum* were more freely branching than plants of 'Sunny Amanda'.
2. Plants of the new *Osteospermum* flowered earlier than plants of 'Sunny Amanda'.
3. Plants of the new *Osteospermum* had shorter peduncles than plants of 'Sunny Amanda'.

BRIEF DESCRIPTION OF THE PHOTOGRAPHS

The accompanying photographs illustrate the overall appearance of the new *Osteospermum*. This photographs show the colors as true as it is reasonably possible to obtain in colored reproductions of this type. Colors in the photographs may differ slightly from the color values cited in the detailed botanical description which accurately describe the colors of the new *Osteospermum*.

The photograph on the first sheet comprises a side perspective view of a typical flowering plant of 'Tra Yelbic'.

The photograph on the second sheet is a close-up view of a typical inflorescence of 'Tra Yelbic'.

DETAILED BOTANICAL DESCRIPTION

In the following description, color references are made to The Royal Horticultural Society Colour Chart, 2001 Edition, except where general terms of ordinary dictionary significance are used. The aforementioned photographs, following observations and measurements describe plants grown in 12-cm containers in Hillscheid, Germany during the spring in a greenhouse and under conditions and practices which approximate those generally used in commercial *Osteospermum* production. Measurements and numerical values represent averages for typical flowering plants. Plants were pinched one time and were about four months old when the photographs and description were taken.

Botanical classification: *Osteospermum ecklonis* 'Tra Yelbic'.

Parentage:

*Female, or seed, parent.*—Proprietary selection of *Osteospermum ecklonis* identified as code number OZ-185-1, not patented.

*Male, or pollen, parent.*—Proprietary selection of *Osteospermum ecklonis* identified as code number OY-81-2, not patented.

Propagation:

*Type.*—Terminal vegetative cuttings.

*Time to initiate and develop roots.*—About 18 to 28 days.

*Root description.*—Fibrous; close to 155D in color.

Plant description:

*Plant form/growth habit.*—Compact, semi-upright and mounded plant habit. Inflorescences positioned well above the foliar plane. Vigorous growth habit.

*Plant height, soil level to top of foliar plane.*—About 16 cm.

*Plant height, soil level to top of inflorescences.*—About 16 cm to 18 cm.

*Plant diameter.*—About 23 cm to 24 cm.

*Lateral branches.*—Quantity per plant: Freely branching, about 17 lateral branches per plant; dense and full plants. Length: About 13 cm to 16 cm. Diameter: About 3 mm to 4 mm. Internode length: About 1 cm to 1.5 cm. Strength: Moderately strong. Texture: Smooth, glabrous to slightly hirsute. Color: Close to 143C occasionally with blotches, close to 177A to 177B.

*Foliage description.*—Arrangement: Alternate, simple. Length: About 6 cm to 6.5 cm. Width: About 2.8 cm to 2.9 cm. Shape: Elliptical to oblanceolate. Apex: Broadly acute. Base: Cuneate. Margin: Dentate. Texture, upper and lower surfaces: Pubescent; leathery. Venation pattern: Pinnate. Color: Developing foliage, upper surface: Close to 137B. Developing foliage, lower surface: Close to 137D. Fully expanded foliage, upper surface: Close to 137B to 137C; venation, close to 145A. Fully expanded foliage, lower surface: Close to either 137D or 138A; venation, close to 145A. Petiole length: About 5 mm to 15 mm. Petiole diameter: About 4 mm to 5 mm. Petiole texture, upper and lower surfaces: Hirsute. Color, upper and lower surfaces: Close to 145B.

Inflorescence description:

*Appearance.*—Daisy-type inflorescence form with narrowly elliptic-shaped ray florets. Inflorescences positioned above the foliage, arising from leaf axils. Disc and ray florets developing acropetally on a capitulum. Inflorescences face mostly upright. Freely flowering habit; numerous inflorescences develop over time per plant. Inflorescences persistent. Inflorescences not fragrant.

*Flowering response.*—In Germany, plants of the new *Osteospermum* flower recurrently to continuously from spring to autumn. Early flowering habit, plants begin flowering about nine to ten weeks after planting. Inflorescences last about 12 to 15 days on the plant.

*Inflorescence bud.*—Height: About 1.2 cm to 1.5 cm. Diameter: About 8 mm to 11 mm. Shape: Ovate. Color: Close to N144A.

*Inflorescence size.*—Diameter: About 5.5 cm to 6 cm. Depth (height): About 1.5 cm to 2 cm. Disc diameter: About 1.2 cm to 1.3 cm.

*Ray florets.*—Length: About 3.2 cm to 3.4 cm. Width: About 9 mm to 11 mm. Shape: Narrowly elliptical. Apex: Obtuse, occasionally very slightly emarginate. Base: Attenuate. Margin: Entire. Texture, upper and lower surfaces: Papillose. Orientation: Roughly perpendicular to the peduncle. Number of ray florets per inflorescence: About 19 to 26 in two whorls; ray florets imbricate. Color: When opening, upper surface: Close to 10A; towards the apex, close to 12A to 12B. When opening, lower surface: Close to 151A; towards the margins, close to 6C. Fully opened, upper surface: Apex to mid-section, close to 12A to 12C; towards the base, close to 4D; at the base, close to 77B. Fully opened, lower surface: Close to 158D; towards the margins, close to either 11A or 12B.

*Disc florets.*—Length: About 4 mm to 6 mm. Diameter: About 1 mm to 1.5 mm. Shape: Tubular with five lobes at the apex. Apex: Broadly acute to obtuse. Number of disc florets per inflorescence: About 60 to 80. Color: Immature: Close to 146D. Mature: Close to 4D; at the apex, close to 8D.

*Phyllaries.*—Length: About 9 mm to 12 mm. Width: About 2 mm to 3 mm. Shape: Ligulate to lanceolate.

Apex: Acuminate. Base: Fused. Margin: Entire. Texture, upper surface: Smooth, glabrous. Texture, lower surface: Densely pubescent. Quantity per inflorescence: About 19 to 22 in two whorls; phyllaries slightly imbricate. Color, upper and lower surfaces: Close to 137B.

*Peduncles.*—Length: About 3 cm to 5 cm. Diameter: About 2 mm to 3 mm. Strength: Strong. Texture: Hirsute. Color: Between 143C to 144B.

*Reproductive organs.*—Androecium: Present on disc florets only. Stamen length: About 5 mm to 6 mm. Stamen color: Close to 200A. Pollen amount: Abundant. Pollen color: Close to 17A. Gynoecium: Present on ray florets only. Pistil length: About 4 mm to 5 mm. Stigma color: Close to 200A. Style length: About 3 mm to 4 mm. Style color: Close to 145D.

*Seeds/fruits.*—Seed and fruit development have not been observed.

Disease/pest resistance: Plants of the new *Osteospermum* have not been shown to be resistant to pathogens and pests common to *Osteospermums.*

Garden performance: Plants of the new *Osteospermum* have been observed to have good garden performance and to tolerate rain, wind and temperatures ranging from about 1° C. to about 35° C.

It is claimed:

1. A new and distinct *Osteospermum* plant named 'Tra Yelbic' as illustrated and described.

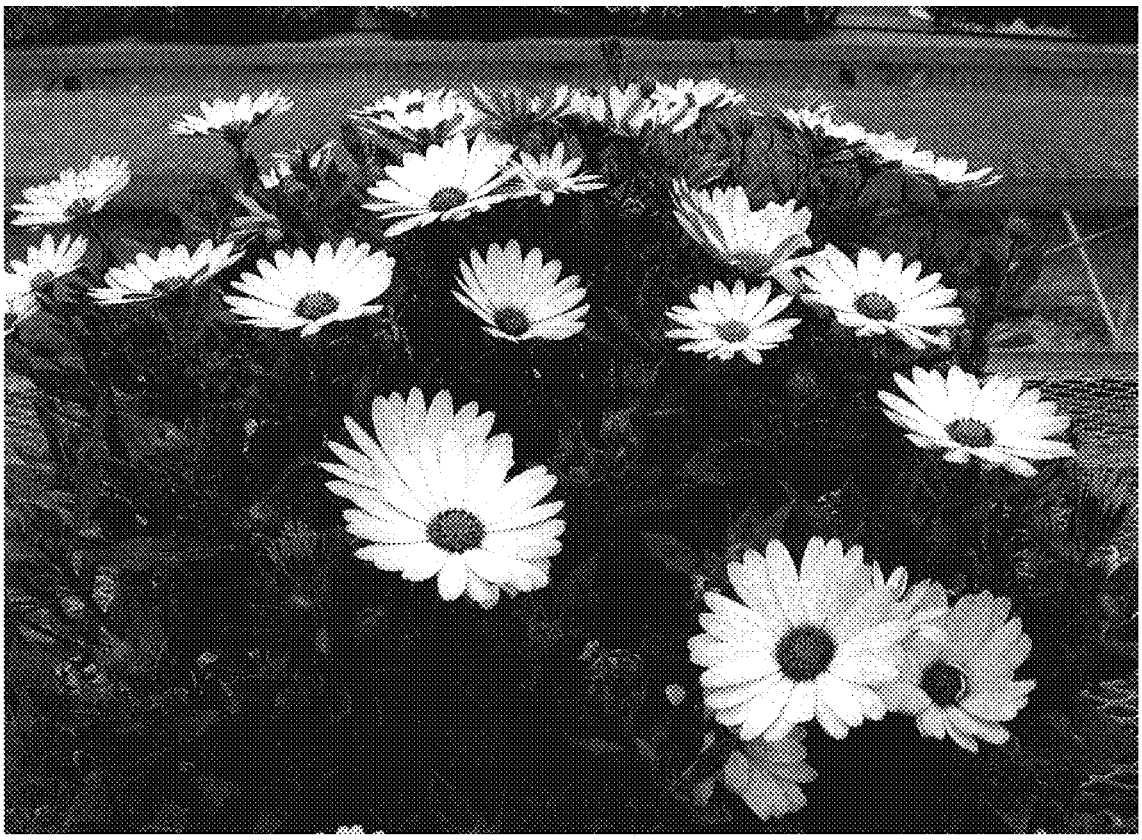

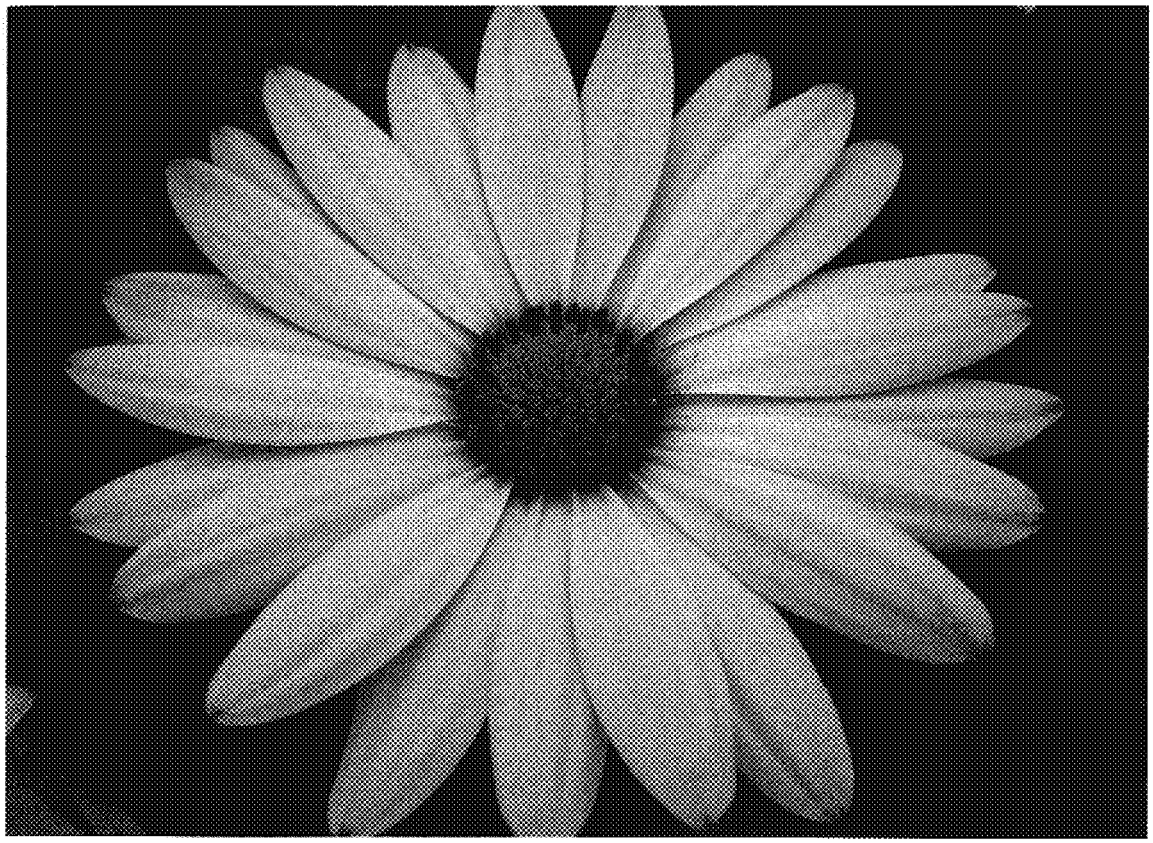

* * * * *